(12) United States Patent
Falsetti et al.

(10) Patent No.: US 9,213,019 B2
(45) Date of Patent: Dec. 15, 2015

(54) METHOD OF DETERMINING A SIZE OF A DEFECT USING AN ULTRASONIC LINEAR PHASED ARRAY

(75) Inventors: Robert Vincent Falsetti, Schnectady, NY (US); Gary Austin Lamberton, Glenville, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 888 days.

(21) Appl. No.: 13/299,504

(22) Filed: Nov. 18, 2011

(65) Prior Publication Data

US 2013/0132002 A1    May 23, 2013

(51) Int. Cl.
| | |
|---|---|
| G01B 17/00 | (2006.01) |
| G01N 29/26 | (2006.01) |
| G01N 29/06 | (2006.01) |
| G01N 29/22 | (2006.01) |
| G01N 29/265 | (2006.01) |

(52) U.S. Cl.
CPC ............ *G01N 29/262* (2013.01); *G01N 29/069* (2013.01); *G01N 29/221* (2013.01); *G01N 29/265* (2013.01); *G01N 2291/0289* (2013.01); *G01N 2291/106* (2013.01)

(58) Field of Classification Search
CPC ............ H01L 41/316; G02F 1/133553; G02F 1/133555; G10K 11/352
USPC ............................... 73/382, 602, 608; 702/39
See application file for complete search history.

(56) References Cited

U.S. PATENT DOCUMENTS

| | | | | |
|---|---|---|---|---|
| 3,585,851 | A * | 6/1971 | Walther | 73/624 |
| 4,730,495 | A * | 3/1988 | Green | 73/620 |
| 7,263,888 | B2 * | 9/2007 | Barshinger et al. | 73/606 |
| 7,987,724 | B2 * | 8/2011 | Takada | 73/641 |
| 8,672,850 | B1 * | 3/2014 | Miller | 600/447 |

(Continued)

OTHER PUBLICATIONS

Search Report and Written Opinion from corresponding EP Application No. 12192567.1-1554 dated Feb. 25, 2013.

(Continued)

*Primary Examiner* — Paul D Lee

(57) ABSTRACT

A method and apparatus for determining a dimension of a defect in a component is disclosed. A linear array of acoustic transducers is used to propagate a focused ultrasonic beam along a first focal line. The focused ultrasonic beam is moved across the defect in a first array direction substantially perpendicular to the first focal line. The dimension of the defect is determined from at least one reflection of the focused ultrasonic beam from the defect as the focused ultrasonic beam moves across the defect.

15 Claims, 4 Drawing Sheets

(56) References Cited

U.S. PATENT DOCUMENTS

| | | |
|---|---|---|
| 2002/0081494 A1* | 6/2002 | Kondo et al. ............... 429/224 |
| 2004/0050166 A1* | 3/2004 | Batzinger et al. ............ 73/614 |
| 2005/0022602 A1 | 2/2005 | Falsetti et al. |
| 2006/0048576 A1* | 3/2006 | Kiuchi et al. ............... 73/593 |
| 2006/0255019 A1* | 11/2006 | Martukanitz et al. .... 219/121.64 |
| 2008/0314153 A1* | 12/2008 | Langlois et al. ............ 73/606 |
| 2009/0078742 A1 | 3/2009 | Pasquali et al. |
| 2009/0235749 A1 | 9/2009 | Ehara et al. |
| 2009/0255341 A1 | 10/2009 | Zimmerman et al. |
| 2009/0320584 A1 | 12/2009 | Lund et al. |
| 2010/0251821 A1 | 10/2010 | Mizota et al. |
| 2010/0329081 A1 | 12/2010 | Sullivan et al. |
| 2011/0232386 A1 | 9/2011 | Ito et al. |

OTHER PUBLICATIONS

Komura, I. et al., "Crack detection and sizing technique by ultrasonic and electromagnetic methods", Nuclear Engineering and Design, Amsterdam, NL, vol. 206, No. 2-3, pp. 351-362, Jun. 1, 2001.

Drinkwater, B. W. et al., "Ultrasonic arrays for non-destructive evaluation: A review", NDT & E International, Butterworth-Heinemann, Oxford, GB, vol. 39, No. 7, pp. 525-541, Oct. 1, 2006.

Satyanarayan, L. et al., "Sizing Cracks in Power Plant Components Using Array Based Ultrasonic Techniques", Journal of Nondestructive Evaluation, Kluwer Academic Publishers—Plenum Publishers, NE, vol. 28, No. 3-4, pp. 111-124, Aug. 4, 2009.

\* cited by examiner

METHOD OF DETERMINING A SIZE OF A DEFECT USING AN ULTRASONIC LINEAR PHASED ARRAY

BACKGROUND OF THE INVENTION

The subject matter disclosed herein relates to methods of determining a size of a defect. Various components, for example turbine components used in power generation, require the ability to operate under high stress. Welds are potential sources of weakness in a component due to the potential number and size of defects present. One method of determining the size of defects includes directing sound beams focused to a small point towards the particular defect. Some methods for producing such sound beams include reducing the size of a transducer that produces the sound beam, using lenses to focus a sound beam, and using a two-dimensional phased array to focus the beam. These methods can be complex and costly. The present disclosure provides a method and apparatus for determining a size of a defect using an ultrasonic linear phased array.

BRIEF DESCRIPTION OF THE INVENTION

According to one aspect of the invention, a method of determining a dimension of a defect in a component is disclosed that includes propagating a focused ultrasonic beam along a first focal line; moving the focused ultrasonic beam across the defect in a first array direction; and determining the dimension of the defect from at least one reflection of the focused ultrasonic beam from the defect as the focused ultrasonic beam moves across the defect.

According to another aspect of the invention, an apparatus for determining a dimension of a defect of a component is disclosed that includes a linear array of acoustic transducers configured to propagate a focused ultrasonic beam along a first focal line and obtain at least one reflection of the focused ultrasonic beam from the defect; a control unit configured to move the focused ultrasonic beam across the defect to obtain the at least one reflection, and a processor configured to determine the dimension of the defect from the obtained at least one reflection.

These and other advantages and features will become more apparent from the following description taken in conjunction with the drawings.

BRIEF DESCRIPTION OF THE DRAWING

The subject matter, which is regarded as the invention, is particularly pointed out and distinctly claimed in the claims at the conclusion of the specification. The foregoing and other features, and advantages of the invention are apparent from the following detailed description taken in conjunction with the accompanying drawings in which:

The detailed description explains embodiments of the invention, together with advantages and features, by way of example with reference to the drawings.

DETAILED DESCRIPTION OF THE INVENTION

Figure 1:
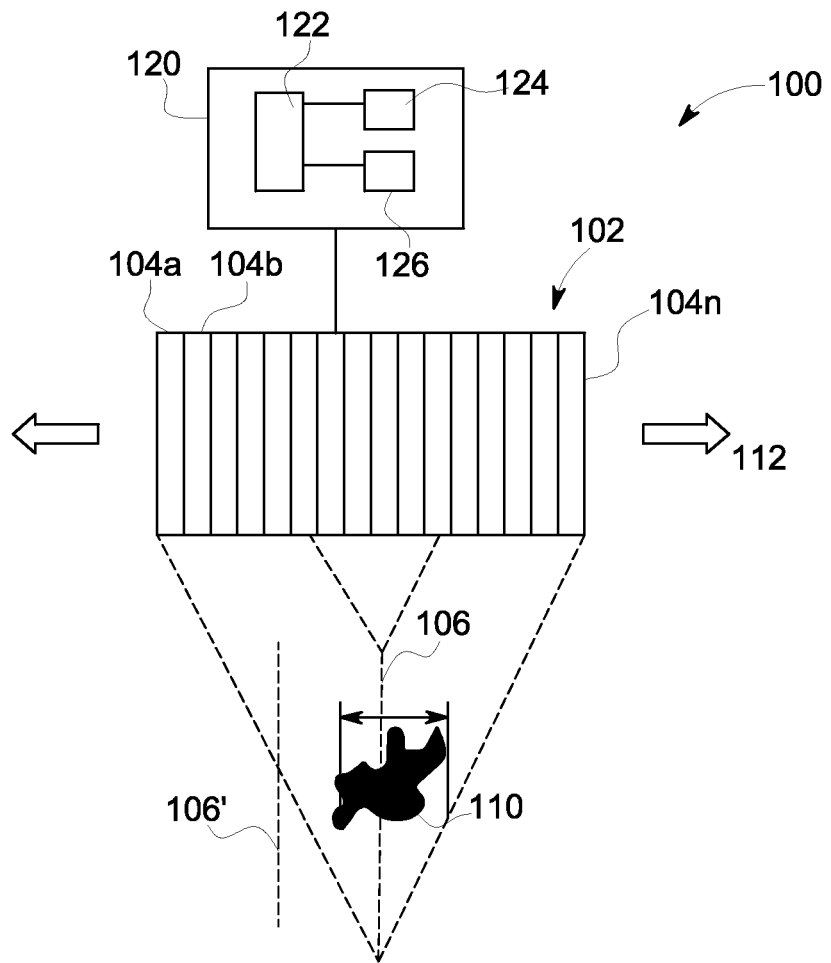
FIG. 1 shows an exemplary apparatus for determining a dimension of an object such as a component defect according to an embodiment of the present disclosure.

FIG. 1 shows an exemplary apparatus 100 for determining a dimension of an object such as a component defect according to an embodiment of the present disclosure. The apparatus 100 includes a linear array, such as linear phased array 102, of ultrasonic transducers $104a \ldots 104n$ aligned along a particular direction, such as exemplary array direction 112. In one embodiment, the ultrasonic transducers can be piezoelectric transducers, which can be activated to produce an ultrasonic wave in response to an applied electrical signal. In another aspect, the transducers are configured to detect ultrasonic waves and to produce an electrical signal in response to the detected waves. The transducers are substantially aligned in a direction generally referred to as an array direction 112. A control unit 120 is coupled to the linear array to operate the ultrasonic transducers. In one aspect, the control unit 120 provides a signal to at least one transducer for activating the transducer and receives a signal from at least one transducer. The control unit includes a processor 122, and a data storage device (also referred to as a computer-readable medium) 124 for storing data and computer programs 126 accessible to the processor 122 for performing various functions disclosed herein, including activation of the transducers and processing of signals obtained from the transducers. The data storage device 124 may be any suitable device, including, but not limited to, a read-only memory (ROM), a random-access memory (RAM), a flash memory, a magnetic tape, a hard disc and an optical disk. In one aspect, the control unit 120 activates the ultrasonic transducers according to an activation sequence selected to produce a focused ultrasonic beam. The focused ultrasonic beam propagates in a substantial line or cylinder along the direction indicated by focal line 106. The use of the term "focal line" can therefore be understood to refer to a focused ultrasonic beam or a propagation path of the focused ultrasonic beam. The activation sequence activates the transducers such that wavefronts produced at the individual transducers arrive substantially simultaneously at focal line 106 to construct the focused ultrasonic beam. In a typical activation sequence, transducers at the ends of the linear array, i.e., $104a$ and $104n$, are the first to be activated, followed by the next transducers sequentially in from the ends, (i.e., $104b$ and $104n-1$) and so on until the middle transducer(s) are activated. The focal line 106 is thus directed outward from the linear as if propagating from the middle transducer(s). The transducers can also be activated at individual power levels selected to shape the focused ultrasonic beam. Additionally, another focused ultrasonic beam can be created that propagates along an exemplary focal line 106' parallel to focal line 106 by activating the transducers using a different activation sequence centered around parallel focal line 106'. Any number of focal lines parallel to focal line 106 can therefore be created using an appropriate activation sequence.

In one aspect of the present disclosure, the focused ultrasonic beam is moved across a defect, for instance, along array direction 112. Motion of the focal line 106 (and hence of the focused ultrasonic beam) along direction 112 can be simulated by create a plurality of parallel focal lines using the methods discussed above. The order of creation of the parallel focal lines is in a particular direction, such as from left to right. Alternatively, the focal line 106 can be moved along direction 112 by propagating a single focal line 106 and moving the linear phased array 102 itself along array direction 112. In either case, position of the focal line can be measured and recorded for subsequent calculations.

As shown in FIG. 1, the focal line 106 is directed toward a defect 110. The defect can be a structural defect or a defect in a material, but can apply equally to any object within a component that reflects the focused ultrasonic beam. In various embodiments, the structure can be a turbine component, such as a rotor turbine, a gas turbine shell, a compressor shell casing, an aviation rotor, and welded rotor, etc. Typical structures include turbine and generator components. In exemplary embodiments, the defect is a weld defect which can be, for example, slag or a non-metallic inclusion, such as such as tungsten, quartz or other materials used in welding processes. In alternate embodiments, the defect can be a crack formation or pore formation in the weld, for example. Typically, the focal line 106 is swept along direction 112 to cross a surface of the defect 110. When the focal line 106 is moved across the defect, the focused ultrasonic beam reflects off of the defect 110 back toward the linear array 102. The received reflections can be sent to the exemplary control unit 120 for processing.

The reflection measured as the focal line is moved along a particular direction is used to determine a size of the defect in the particular direction. The dimension of the defect is typically determined by determining locations of the focal line at which reflection intensity decreases by a selected amount, such as to a half amplitude of the peak amplitude or a −6 dB drop intensity. If the focused ultrasonic beam (i.e., focal line 106) has a width smaller than the defect being measured, then the location at which a drop of reflection intensity of at least −6 dB occurs as the focal line 106 is moved over the defect 110 can be used to determine the dimension of the defect. If the defect is smaller than the width of the focused beam, then an upper bound of the defect size can be inferred by comparing reflection intensities to intensities obtained from calibration reflectors of known size.

Figure 2:
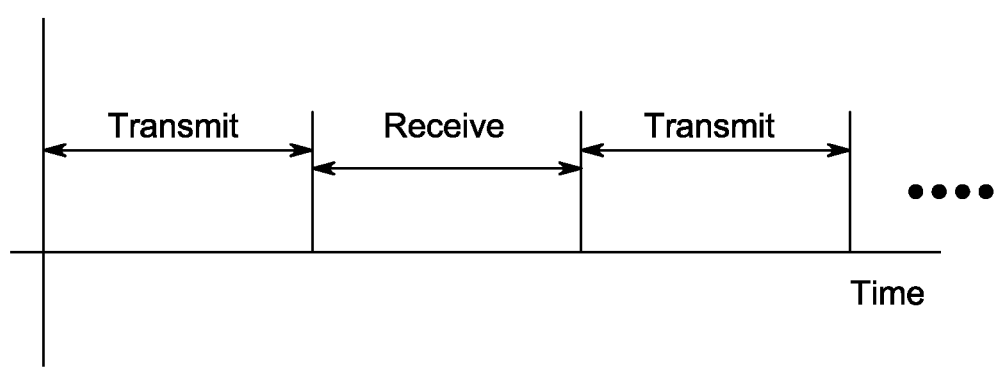
FIG. 2 shows an exemplary timing sequence for operating the exemplary apparatus of FIG. 1.

FIG. 2 shows an exemplary timing sequence for operating the linear phased array 102 in one embodiment of the present disclosure. The linear array 102 can be operated in an alternating set of modes, such as a transmission mode 201 for propagating a focused ultrasonic beam and a reception mode 202 for detecting reflections of the focused ultrasonic beam from the defect. The duration of the reception mode can be selected by the control unit and generally can be selected and/or altered to accommodate an expected travel time of the focused ultrasonic beam to and from the defect.

Figure 3:
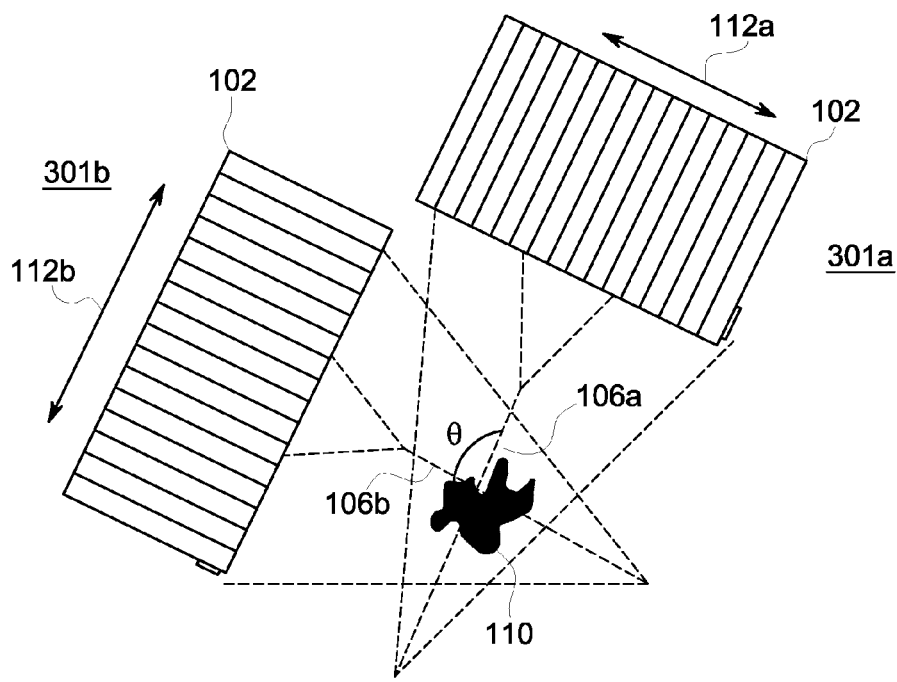
FIG. 3 shows various orientations of an exemplary linear phased array with respect to a defect.

FIG. 3 shows various orientations of an exemplary linear phased array 102 with respect to a defect 110. The linear array can be oriented and translated so that the focused ultrasonic beam impinges on the defect from various directions in order to obtain two-dimensional measurements of the defect. At a first location 301a, linear phased array 102 is oriented to propagate a focused ultrasonic beam along a focal line 106a in a first direction towards the defect. The focal line 106a is moved along first array direction 112a substantially perpendicular to the focal line 106a. Reflections of the focused ultrasonic beam therefore yield information of the dimension of the defect along first array direction 112a. At a second location 301b, the linear array 102 is oriented about 90 degrees from its orientation at first location 301a to provide a focal line 106b that impinges on the defect 110 from a second direction. In an exemplary embodiment, the second focal line 106b is substantially perpendicular to the first focal line 106a and is moved along second array direction 112b to obtain a dimension of the defect along second array direction 112b. Although the second location 301b as shown in FIG. 3 is selected so that the second focal line is 106b is substantially perpendicular the first focal line 106a, this is not meant as a limitation of the disclosure. The second location can be any location angularly separated from the first location 301a along angle θ in order to obtain dimensions from any direction. Additionally, measurements can be taken from a third location that is out of the plane defined by the first focal line 106a and the second focal line 106b in order to obtain three dimensions of measurements.

Figure 4:
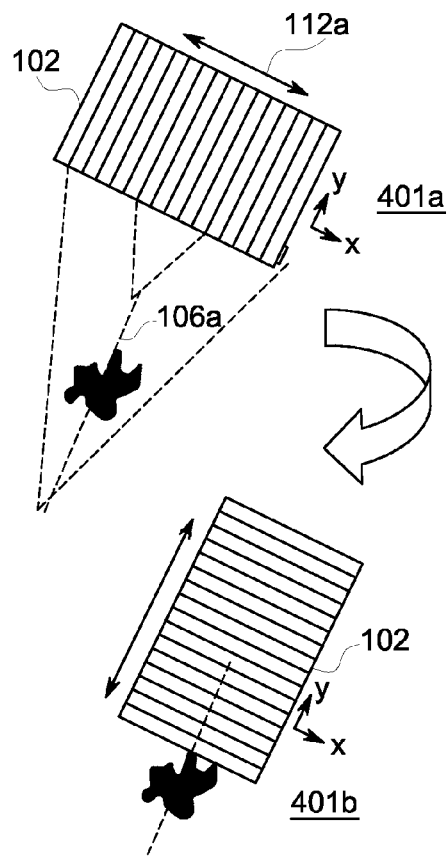
FIG. 4 illustrates a rotation of a linear array about a focal line in another aspect of the present disclosure.

FIG. 4 illustrates a rotation of a linear array about a focal line in another aspect of the present disclosure. In the exemplary rotation of FIG. 4, linear array is rotated from a first orientation 401a to a second orientation 401b. In the first orientation 401a, the array direction is along the x-direction of the shown coordinate system. In the second orientation 401b, the array direction is along the y-direction of the coordinate system. These orientations enable measuring the dimension of the defect along orthogonal directions using the methods discussed herein. Although only two orientations are shown in FIG. 4, this is not meant as a limitation of the disclosure. The linear array can be rotated through any angle. Rotating through 180 degrees allows obtaining a cross-sectional measurement of the defect in the any direction in the plane perpendicular to the direction of the focal line.

Figure 5:
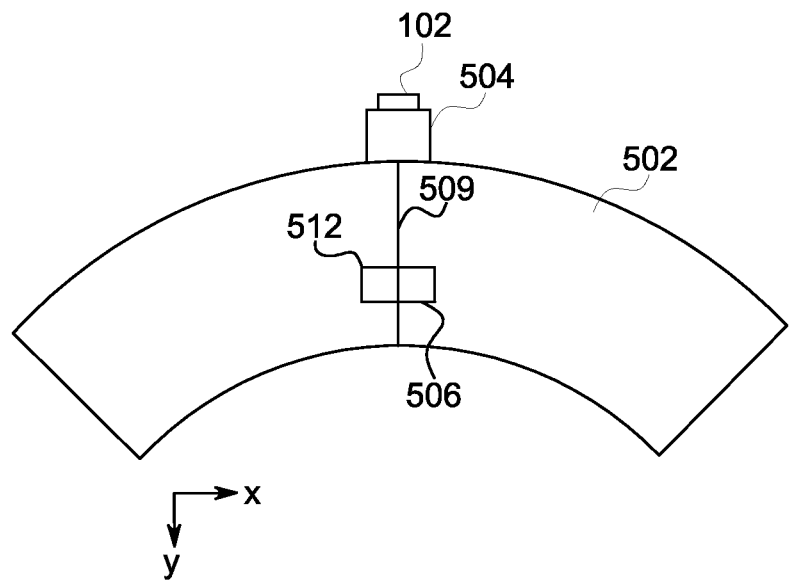
FIG. 5 illustrates use of an exemplary linear phased array of the present disclosure with respect to a component for determining dimensions of a defect in the component.
Figure 6:
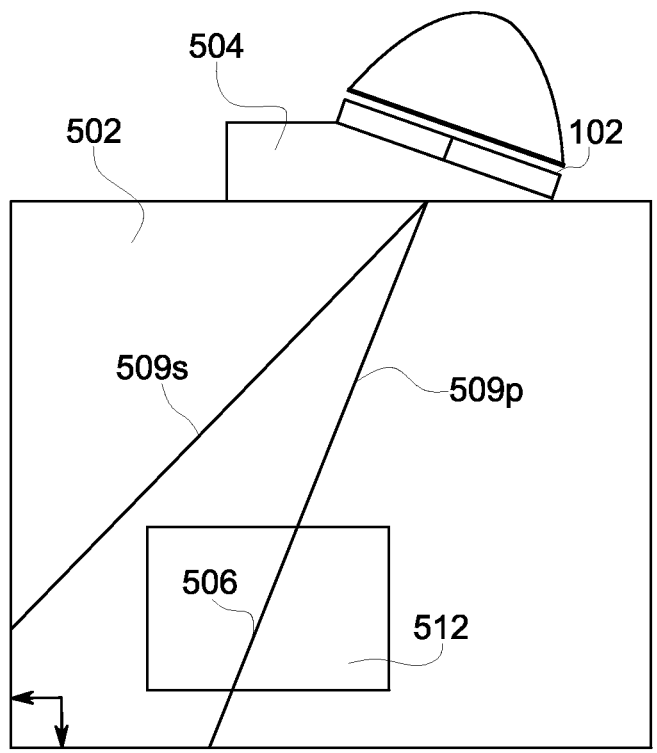
FIG. 6 shows a side view of the exemplary linear phased array of FIG. 5.

FIG. 5 illustrates use of the exemplary linear phased array of the present disclosure with respect to a component for determining dimensions of a defect in the component. The component 502 is shown having a defect 506 at a non-surface location within the component. The defect is indicated by pixels in a reflection intensity map 512. Linear phased array 102 is mounted on an incline of wedge 504 placed in contact with the component 502. In general, a weld will obstruct a beam propagating from a linear array that is placed directly above the weld. Therefore, wedge 504 enables an operator to direct the focused ultrasonic beam toward the defect from an unobstructed side direction. In addition, the wedge 404 can be used to direct the focused ultrasonic beam from the various directions and rotation angles discussed in FIGS. 3 and 4. Directing of the focused ultrasonic beam can also be performed using various alternate methods. The focused ultrasonic beam 509 propagates from the linear phased array 102 through wedge 504 and is directed towards the defect 506. FIG. 6 shows a side view of the linear phased array of FIG. 5. As shown in FIG. 6, focal line 509 comprises both longitudinal waves 509p and shear waves 509s. Typically, the shear waves 509s are used for the purposes of the present disclosure.

In one aspect, the defect 506 can be located using the linear phased array in an unfocused mode to produce an unfocused beam. Other methods known in the art for locating defects can also be used. Once the defect is located, the linear phased array can be focused to provide a focused ultrasonic beam to determine dimensions. In another aspect, the invention can be automated to provide both array rotation and translation indexing. With such an arrangement the reflection data can be reconstructed along lines perpendicular to the beam line focus to produce an image at a selected resolution.

Figure 7:
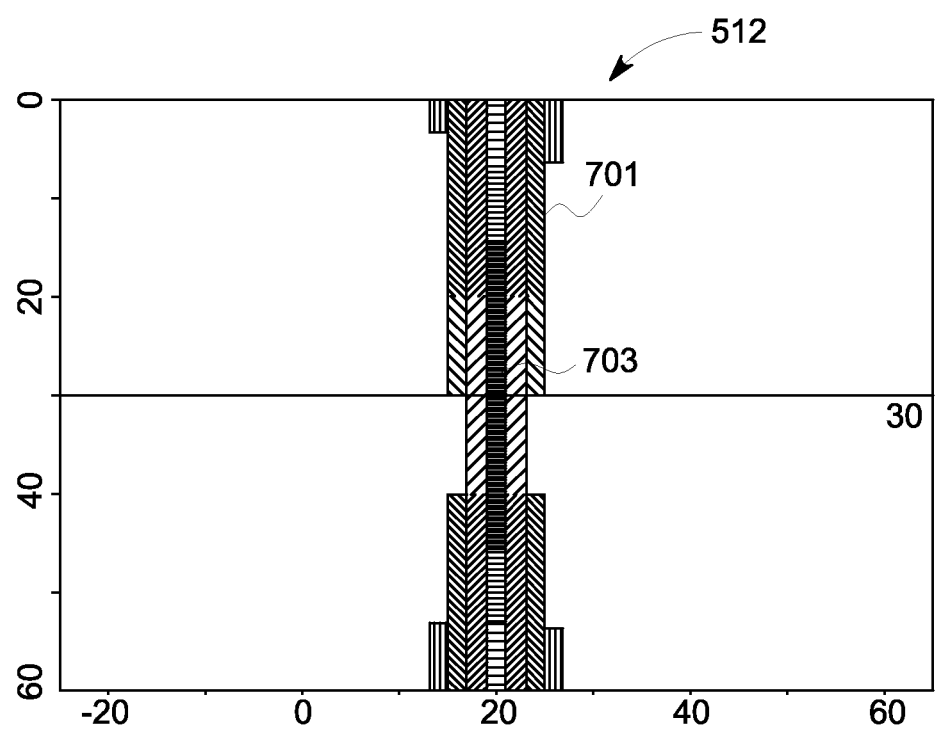
FIG. 7 show an exemplary reflection map obtained from a defect using the methods discussed herein.

FIG. 7 show a detailed view of an exemplary reflection map 512 of a defect obtained using the methods discussed herein. Light pixel 601 and dark pixel 603 are shown. The lightness/darkness of a pixel is indicative of the reflection intensity from a particular location associated with the pixel and can be therefore be used to determine defect size. In alternate embodiments, reflection intensity can be indicated by color or any selected coding method.

Therefore, in one aspect, the present disclosure provides a method of determining a dimension of a defect in a component that includes propagating a focused ultrasonic beam along a first focal line; moving the focused ultrasonic beam across the defect in a first array direction; and determining the dimension of the defect from at least one reflection of the focused ultrasonic beam from the defect as the focused ultrasonic beam moves across the defect. The dimension can be determined by determining a location of the first focal line at which an intensity of the at least one reflection decrease by a selected amount. In various embodiments, the selected amount is at least a half amplitude off of a peak reflection intensity. A linear array of ultrasonic transducers is generally activated to propagate the focused ultrasonic beam. The focused ultrasonic beam can be moved by either moving the linear array or by activating the ultrasonic transducers using a plurality of timing sequences. The linear array can be operated in one of a transmission mode for propagating the focused ultrasonic beam and a reception mode for detecting the at least one reflection. An ultrasonic transducer of the linear phased array can be activated at a selected power level. In one embodiment, a second dimension of the defect can be determined by moving the focused ultrasonic beam along a second array direction that is non-parallel to first array direction. In an alternate embodiment, a second dimension of the defect can be determined by propagating the focused ultrasonic beam along a second focal line that is non-parallel with the first focal line. A two-dimensional area of the defect can therefore be determined for the first and second determined dimensions. A wedge prism can be used to orient the focused ultrasonic beam towards the defect from a direction unobstructed by a weld of the component.

In another aspect, the present disclosure provides an apparatus for determining a dimension of a defect of a component, the apparatus including a linear array of acoustic transducers configured to propagate a focused ultrasonic beam along a first focal line and obtain at least one reflection of the focused ultrasonic beam from the defect; a control unit configured to move the focused ultrasonic beam across the defect to obtain the at least one reflection, and a processor configured to determine the dimension of the defect from the obtained at least one reflection. The processor is further configured to determine a location of the focused ultrasonic beam at which an intensity of the at least one reflection decreases by a selected amount, which in one embodiment is at least half amplitude off of from a peak reflection intensity. The control unit is configured to move the focused ultrasonic beam either by moving the linear array or by activating the ultrasonic transducers using a plurality of timing sequences. The control unit is configured to operate the linear phased array in one of a transmission mode for propagating the focused ultrasonic beam and a reception mode for receiving the at least one reflection. The processor is configured to activate an ultrasonic transducer of the linear phased array at a selected power level. In one embodiment, the linear phased array is configured to rotate to move the focused ultrasonic beam along a second array direction that is non-parallel to first array direction. In another embodiment, the linear phased array is configured to be moved to propagate the focused ultrasonic beam towards the defect along a second focal direction that is non-parallel with the first focal line. The processor can determine a two-dimensional area of the defect from the determined first and second dimensions.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

The invention claimed is:

1. A method of determining a dimension of a defect in a component, comprising:
   activating a linear array of ultrasonic transducers to propagate a focused ultrasonic beam along a first focal line perpendicular to the linear array;
   moving the focused ultrasonic beam across the defect in a first array direction while maintaining the first focal line perpendicular to the linear array;
   rotating the linear array;
   activating the linear array to propagate the focused ultrasonic beam along a second focal line perpendicular to the linear array and moving the focused ultrasonic beam across the defect along a second array direction that is non-parallel to the first array direction while maintaining the second focal line perpendicular to the linear array; and
   determining, by a processor, a distance between locations at which the reflection intensity of the focused ultrasonic beam reduces by a selected amount from a peak intensity of the focused ultrasonic beam in order to determine the dimension of the defect.

2. The method of claim 1, further comprising determining locations at which the intensity of the at least one reflection decreases by one of: (i) at least half of a peak reflection intensity; and (ii) a −6 decibel drop in intensity.

3. The method of claim 1, wherein moving the focused ultrasonic beam further comprises one of: (i) moving the linear array; and (ii) activating the ultrasonic transducers using a plurality of timing sequences.

4. The method of claim 1, further comprising operating the linear array in one of a transmission mode for propagating the focused ultrasonic beam and a reception mode for detecting the at least one reflection.

5. The method of claim 1, wherein an ultrasonic transducer of the linear array is activated at a selected power level.

6. The method of claim 1, further comprising determining a second dimension of the defect by propagating the focused ultrasonic beam along a second focal line that is non-parallel with the first focal line.

7. The method of claim 1, further comprising determining a two-dimensional area of the defect.

8. The method of claim 1, further comprising using a wedge prism to orient the focused ultrasonic beam towards the defect from a direction unobstructed by a weld of the component.

9. An apparatus for determining a dimension of a defect of a component, comprising:
   a linear array of acoustic transducers configured to propagate a focused ultrasonic beam along a first focal line perpendicular to the linear array and obtain at least one reflection of the focused ultrasonic beam from the defect;

a control unit configured to move the focused ultrasonic beam across the defect in a first array direction and a second array direction that is non-parallel to the first array direction to obtain the at least one reflection while maintaining the first focal line perpendicular to the linear array and to rotate the linear array between the first array direction and the second array direction, and a processor configured to determine a distance between locations at which the reflection intensity of the focused ultrasonic beam reduces by a selected amount from a peak intensity of the focused ultrasonic beam in order to determine the dimension of the defect.

10. The apparatus of claim 9, wherein the processor is further configured to determine locations at which the intensity of the at least one reflection decreases by one of: (i) at least half of a peak reflection intensity; and (ii) a −6 decibel drop in intensity.

11. The apparatus of claim 9, wherein the control unit is configured to move the focused ultrasonic beam by doing one of: (i) moving the linear array; and (ii) activating the ultrasonic transducers using a plurality of timing sequences.

12. The apparatus of claim 9, wherein the control unit is configured to operate the linear array in one of a transmission mode for propagating the focused ultrasonic beam and a reception mode for receiving the at least one reflection.

13. The apparatus of claim 9, wherein the processor is configured to activate an ultrasonic transducer of the linear array at a selected power level.

14. The apparatus of claim 9, wherein the linear array is configured to be moved to propagate the focused ultrasonic beam towards the defect along a second focal direction that is non-parallel with the first focal line.

15. The apparatus of claim 9, wherein the processor is further configured to determine a two-dimensional area of the defect.

* * * * *

UNITED STATES PATENT AND TRADEMARK OFFICE
CERTIFICATE OF CORRECTION

PATENT NO. : 9,213,019 B2
APPLICATION NO. : 13/299504
DATED : December 15, 2015
INVENTOR(S) : Falsetti et al.

It is certified that error appears in the above-identified patent and that said Letters Patent is hereby corrected as shown below:

On the title page, item 75, under "Inventors", in Column 1, Line 1, delete "Schnectady," and insert -- Schenectady, --, therefor.

Signed and Sealed this
Twenty-third Day of August, 2016

Michelle K. Lee
*Director of the United States Patent and Trademark Office*